(12) United States Patent
Carr et al.

(10) Patent No.: US 6,241,664 B1
(45) Date of Patent: Jun. 5, 2001

(54) NEEDLE AND NEEDLE PROBE

(75) Inventors: John Christopher Carr, Horsell; Dermot John O'Connor, Ascot; Peter Robert Dennis Styles, Bramley, all of (GB)

(73) Assignee: Medelec Limited, Surrey (GB)

( * ) Notice: Subject to any disclaimer, the term of this patent is extended or adjusted under 35 U.S.C. 154(b) by 0 days.

(21) Appl. No.: 09/331,862

(22) Filed: Jun. 11, 1999

Related U.S. Application Data

(63) Continuation of application No. PCT/GB97/03405, filed on Dec. 10, 1997.

(30) Foreign Application Priority Data

Dec. 13, 1996 (GB) .................................................. 9625894

(51) Int. Cl.[7] .................................................. A61B 5/0492
(52) U.S. Cl. .......................................................... 600/372
(58) Field of Search ..................................... 600/377, 373, 600/372

(56) References Cited

U.S. PATENT DOCUMENTS 5,170,788 * 12/1992 Blumenfeld .
5,452,716 * 9/1995 Clift .

* cited by examiner

Primary Examiner—Scott M. Getzow
(74) Attorney, Agent, or Firm—Darby & Darby

(57) ABSTRACT

A needle (1) and needle probe are provided. The needle (1) has a conducting inner core (12) separated for a conducting outer cannula (14) by an insulating element (16). A first end of the needle is for insertion into a patient, whereas the second end (6) is adapted for electrical connection to the remainder of the instrument. The second end (6) is formed in a substantially conical or substantially pyramidal shape. The inner core (12) at the second end contacts a contact plate (45) of a spring contact probe (22) to provide one electrical contact. To provide the other electrical contact, the outer cannula (16) at the second end is connected to an inner wall (18) which contacts spring fingers (51) mounted around the spring contact probe (22).

15 Claims, 2 Drawing Sheets

NEEDLE AND NEEDLE PROBE

This is a continuation of International Application Serial No. PCT/GB97/03405, filed Dec. 10, 1997.

FIELD OF THE INVENTION

The present invention relates to a needle for use in a needle probe for measurement of electrical activity in a patient. The invention also relates to a needle probe comprising such a needle. The invention relates particularly to a needle and needle probe suitable for use in electromyography (EMG).

BACKGROUND OF THE INVENTION

In EMG, the electrical activity of muscle tissue is recorded and interpreted. When a muscle fibre contracts, a potential is generated. Signals from a given muscle, or group of muscles, can be detected by use of an appropriately situated electrode. This is generally achieved by use of a needle probe having a conducting inner core fixed within a conducting outer cannula, the two being insulated from each other by an intervening insulating layer. The conductive parts of the needle are connected to separate pins of a plug for attachment to the recording equipment. Conventionally, this is achieved by use of separate connecting pins attached to the outer cannula and attached to the inner core, which generally consists of a metal wire.

During an EMG procedure, it is often necessary to use such a probe to take a number of measurements for a single patient. However, to reduce risk of infection to patients, it is desirable to dispose of a needle altogether after it has been used for one patient. This is an expensive procedure if conventional needle probes are used, as several manufacturing stages are required to produce the needle probe, which comprises not only a needle but also an electrical plug. It is thus desirable to provide a new design of needle probe in which new needles can be used for each patient without there being a need to replace an expensive part each time that this is done.

A potential line of development is to simplify the disposable part. This however poses difficulty, because of the need to provide reliable electrical connection between the plug of the probe and, separately, the inner core and the outer cannula.

OBJECT OF THE INVENTION

Accordingly the invention provides a needle for a needle probe for measurement of electrical activity in a patient, comprising: an electrically conducting core; an electrically conducting outer cannula; and an insulating element electrically insulating the core from the outer cannula; wherein the needle has a first end for insertion into a patient, and a second end for making electrical connection to a further part of the needle probe, and wherein said second end has a substantially conical or pyramidal shape. Advantageously, said second end is substantially conical and has a semi-vertical angle lying in the range from 20° to 87.5°: alternatively, said second end is substantially pyramidal, preferably pyramidal with a four-sided base, especially where said four-sided base is substantially square and also the angle between each triangular face at said second end and the longitudinal axis of the needle lies in the range from 20° to 87.5°.

It is of benefit if the substantially conical or pyramidal shape of the core is blunted by application of a blunting force to the second end of the needle. Also preferable are that the outer cannula comprises stainless steel and that the insulating layer comprises polyesterimide. Advantageously, the needle further comprises a receiving socket having a conducting inner wall electrically connected to the outer cannula.

There is further provided a needle probe, comprising a needle as indicated above and a further part, wherein the needle is selectively engageable with said further part, said further part having an electrical connector, first means to provide electrical connection between the core and a first connection point of the electrical connector on engagement of the needle with the further part, and second means to provide electrical connection between the outer cannula and a second connection point of the electrical connector on engagement of the needle with the further part. Advantageously, said first means comprises a spring contact probe adapted to press against the core at said second end of the needle when the needle is engaged with said further part of the needle probe, especially where said spring contact probe is adapted to press against said core with a force lying in the range of 52 to 108 gf. Also advantageously, said second means comprises a plurality of resilient fingers adapted to bear against the conducting inner wall of the receiving portion of the needle when the needle is engaged with the further part of the needle probe, especially where said second means comprises six resilient fingers.

The invention therefore solves problems of the prior art by provision of an inexpensive and replaceable needle which can be brought reliably into the necessary electrical contact with a reusable further part of the needle probe.

BRIEF DESCRIPTION OF THE DRAWINGS

Specific embodiments of the present invention are described below, by way of example, with reference to the accompanying drawings, in which.

DETAILED DESCRIPTION OF THE INVENTION

Figure 1:
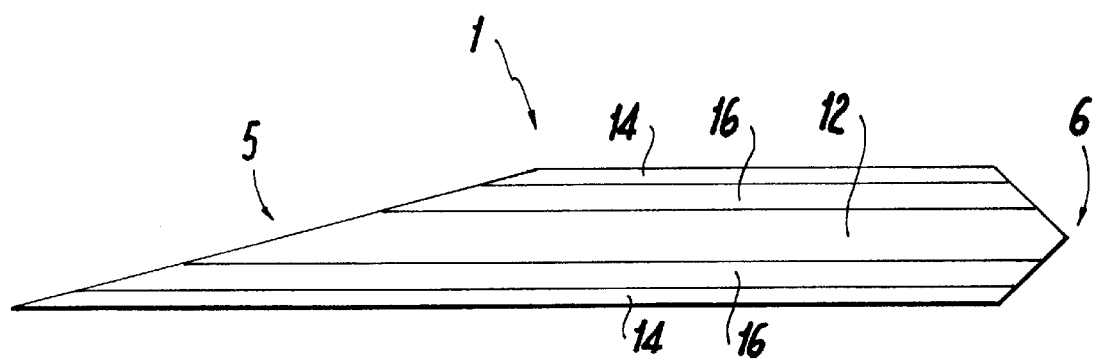
FIG. 1 shows a needle prepared for use as a needle of a needle probe in an embodiment of the present invention.

FIG. 1 shows a needle 1 prepared for use as a needle of a needle probe in an embodiment of the present invention. The needle comprises an electrically conducting core 12 fixed in an electrically conducting outer cannula 14, and also an insulating element 16 electrically insulating the core 12 from the outer cannula 14. The needle has a first end 5 for insertion into a patient: this first end 5 is prepared by conventional means used to prepare needle points for conventional needle probe needles of similar construction. The needle also has a second end 6 of a substantially conical (or alternatively substantially pyramidal) shape to make electrical connection to the remainder of the instrument. A method of preparation for such a second end 6 is discussed below.

Inner core 12 may be formed from a conducting metal wire or rod: platinum is a conventional choice for use as such an inner core. Stainless steel is an advantageous choice for outer cannula 14, for reasons of biocompatibility and structural strength. Strength, electrical properties, and biocompatibility are relevant factors in the choice of material for insulating layer 16: a suitable choice is polyesterimide.

The angle of second end 6 (semi-vertical angle for a conical end) preferably lies within the range of 20° to 87.5°. The choice of angle is discussed further below.

Figure 2:
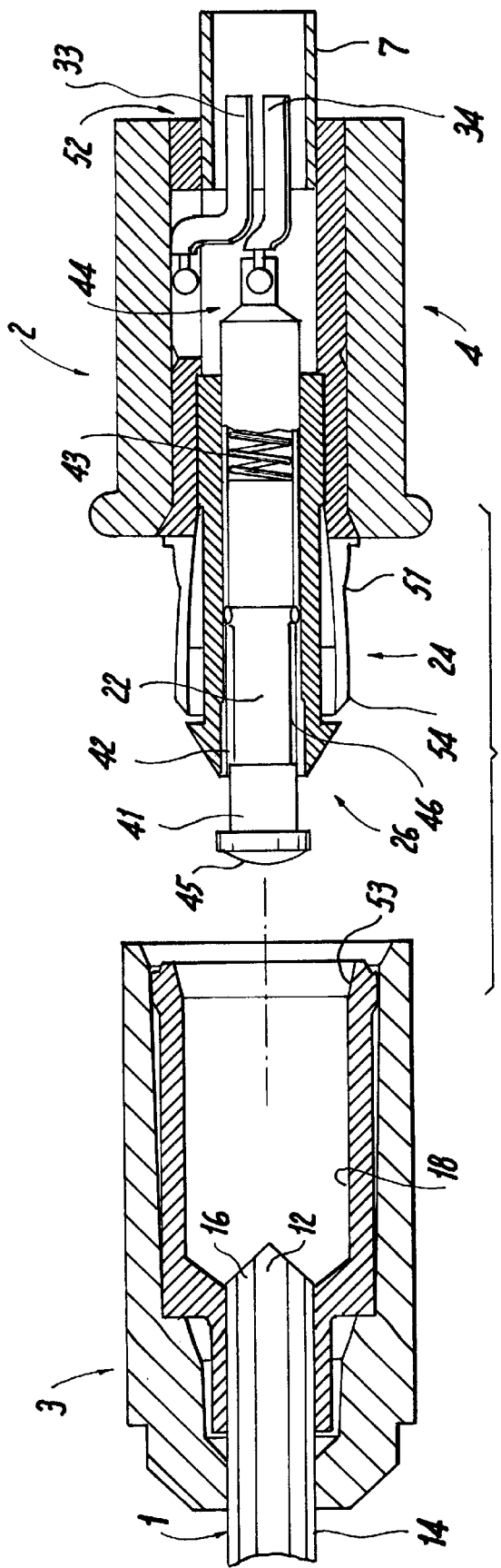
FIG. 2 shows an embodiment of a needle probe according to an embodiment of the present invention.

FIG. 2 shows a needle 1 of a needle probe ready for connection to a further part 2 of the needle probe, all according to an embodiment of the present invention. The needle part 1 is completed by a receiving socket 3. Receiving socket 3 has an inner wall 18 which is electrically conducting. Receiving socket 3 engages around outer cannula 14 such that inner wall 18 of receiving socket 3 is in electrical connection with outer cannula 14 of the needle. Inner wall 18 is isolated electrically from inner core 12.

Further part 2 of the needle probe terminates in a plug 4 for insertion into receiving socket 3. When the plug 4 is fully inserted into receiving part 3, separate low impedance connections are established to the inner core 12 and the outer cannula 14, by means which are discussed below. A lead 7 is connected to plug 4, the lead having a first wire 32 for the electrical connection to inner core 12 and a second wire 33 for the electrical connection to the outer cannula 14 on full insertion of the plug 4 into the receiving part 3. Wires 32,33 may lead to, for example, pins of a plug to be plugged into an EMG recording machine (all not shown).

Electrical connection between inner core 12 and wire 32 is achieved by means of a spring contact probe ("pogo stick contact") 22. Such spring contact probes are conventionally used in testers for printed circuit boards. The spring contact probe comprises a rod 41, terminating in a contact surface 45, and constrained to slide within a sheath 42 against the action of a spring 43. The sheath 42 has a restriction with a diameter less than that of all but a narrowed portion 46 of the rod 41. This constrains the range of motion of the rod 41 and hence also the range of spring force that can be applied from spring 43 through rod 41 to any body contacting plate 45: for a conventional spring contact probe, which is appropriate for use in embodiments of the present invention, this range of spring force is from 52 gf to 108 gf. Completing the spring contact probe is a conducting socket 44 in which sheath 42 is frictionally engageable. The spring contact probe 22 is mounted within an insulating block part 26, and makes a soldered or otherwise secure contact to wire 32.

Electrical connection between outer cannula 14 and wire 33 is achieved by resilient spring contact 24. Resilient contact 24 comprises a collar 52 around the insulating block part 26. Extending from collar 52 in the direction of the needle are a plurality of resilient spring fingers 51: advantageously, there are six of these spring fingers 51, as this leads to a highly stable connection, although arrangements with four or eight spring fingers 51 may also provide some benefit. The arrangement is designed such that the spring fingers 51 are adapted to locate within the inner wall 18 and provide good electrical connection with it. In the specific embodiment, this is achieved by having a sloping face 53 around inner wall 18: the inner diameter of the sloping face 53 is less than that of plug 4 around the tips 54 of spring fingers 51, but the outer diameter of sloping face 53 is greater than the diameter of plug 4 at this point. The effect achieved is that the tips 54 of spring fingers 51 are urged within receiving socket 3 to bear against inner wall 18. The spring fingers 51 thus provide electrical connection to collar 52, which is connected by solder or other secure means to wire 33. The spring fingers 51 are also, in this position of engagement, disposed such that there will be a frictional force between spring fingers 51 and inner wall 18 opposing removal of the plug 4 from the receiving socket 3.

When the plug 4 is fully inserted within the receiving socket 3, the plate 45 of the spring contact probe 22 is in contact with inner core 12 at the second end 6 of the needle 1. Preferably, the dimensions of the various components are selected such that in this position of full engagement, the rod 41 of the spring contact probe 22 is not at either extreme end of its range of travel within the sheath 42, with the result that the force exerted on the end of inner core 12 is within the range of spring force provided by the spring contact probe with no additional compression force such as would be provided if the rod 41 was urged against one of its stop positions. As indicated previously, this spring force lies in the range 52 gf to 108 gf for a conventional spring contact probe, but could readily be varied, if appropriate, by a different choice of spring 43. It is advantageous that on full engagement of the plug 4 into the receiving socket 3, the frictional force acting (between spring fingers 51 and inner wall 18) to prevent disengagement exceeds the force exerted by spring 43, which acts to urge the plug 4 away from the needle 1: otherwise, it is necessary to provide additional retention means to maintain the plug 4 in engagement with the receiving socket 3.

It is necessary for effective operation of the needle probe for a reliable low impedance contact to be achieved between the inner core 12 and the pogo stick contact 22. A number of features are relevant to this aim. Of particular significance is the angled shape of the second end 6 of the needle 1. If this angle is too small, and the second end 6 thus too sharp, there will be an unacceptable risk that the needle 1 will deform at the second end such that inner core 12 short circuits to the outer cannula 14 with the result that the spring contact probe 22 "bridges" and short circuits. If the angle is too large, there will again be an unacceptable risk of a short between inner core 12 and outer cannula 14, which this time would most likely be caused by contact plate 45 contacting both inner core 12 and outer cannula 14. The choice of surface for contact plate 45 is also of relevance: a shallow convex contact surface for plate 45 is of benefit in minimising the risk of short circuit, although a flat contact surface also provides a low risk. The contact between inner core 12 and spring contact probe 22 should have a measure of resilience if a satisfactory low impedance is to be achieved. In part, this resilience is achieved by the nature of the spring contact probe: however, the nature of the inner core 12 at the second end 6 of the needle is also of significance. Significant in choice of material for inner core 12, are suitability of electrical properties and biocompatibility. Malleability can also be advantageous, as one approach to providing a satisfactory low impedance contact to plate 45 of spring contact probe 22 is by use of a core material such that at the second end 6 the tip of inner core 12 will deform under pressure sufficiently to provide a blunted contact surface of extended area. A sufficient degree of deformation to provide a satisfactory low impedance contact may be achieved by a contact force in the range of 52 to 108 gf—in other words, satisfactory deformation can be achieved merely by placing plug 4 into receiving socket 3. However, needles 1 may also be predeformed, for example during a testing process during manufacture, by application of such a force against the tip of inner core 12 at the second end 6 of the needle. Other approaches are also possible for blunting the needle 1 at its second end. Embodiments of the invention may, however, employ needles with sharp rather than blunted second ends 6.

Figure 3:
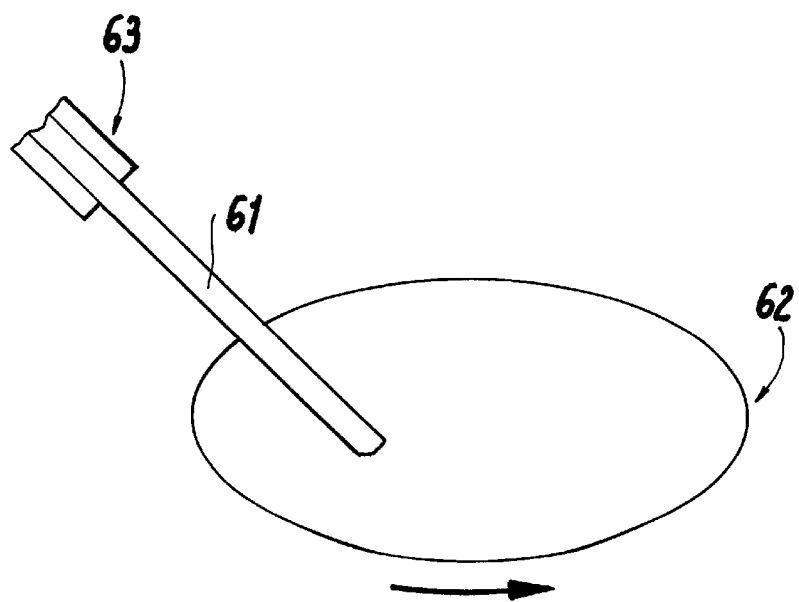
FIG. 3 shows a method of preparing a needle for use as a needle of a needle probe according to an embodiment of the present invention.

FIG. 3 shows in schematic form the preparation of a needle for use as the needle of a needle probe according to embodiments of the present invention. A stock 61 for the needle, comprising a cylinder having an outer core to provide outer cannula 14, an inner core to provide inner core 12, and an insulating member therebetween to provide insulating layer 16, is held within a jig 63. This jig advantageously comprises a chuck for retaining stock 61 which is structurally similar to the chuck of a conventional drafting pencil. The jig 63 is adapted to hold the stock 61 at an angle to a grinding wheel 62. Grinding wheel 62 is adapted to grind needle stock 61 effectively: this requires skilled selection of materials because of the non-uniform construction of stock 61. Advantageously, the wheel 62 is rotated at speeds of approximately 3000 RPM, and a wheel of 600 grit or similar is used. To form a conical point, the chuck of jig 63 and hence needle stock 61 are rotated, advantageously at a speed of approximately 100 RPM. Alternatively, to form a pyramidal point, the chuck of jig 43 is not rotated during grinding, but the chuck (or the jig as a whole) is adapted to move between a series of fixed positions such that the needle stock 61 is brought into contact with the grinding wheel 62 at a fixed number of positions about its own axis (for example, four positions with a 90 degree angular spacing between each to form a square based pyramid), but in each case so that the angle between the stock axis and the grinding wheel 62 remains substantially constant, so each side face of the pyramid is ground with the same angle. In alternative embodiments of the invention, other polygonal bases for the pyramid rather than a square may be used, in which case the arrangements for bringing the needle stock 61 into contact with the grinding wheel 62 will need to be changed accordingly.

What is claimed is:

1. Needle for a needle probe for measurement of electrical activity in a patient, comprising:

an electrically conducting core;

an electrically conducting outer cannula; and an insulating element electrically insulating the core from the outer cannula;

wherein the needle has a first end for insertion into a patient, and a second end for making electrical connection to a further part of the needle probe, and wherein said second end has a substantially conical or pyramidal shape.

2. Needle as claimed in claim 1, wherein said second end is substantially conical and has a semi-vertical angle lying in the range from 20° to 87.5°.

3. Needle as claimed in claim 1, wherein said second end is substantially pyramidal and the angle between each triangular face at said second end and the longitudinal axis of the needle lies in the range from 20° to 87.5°.

4. Needles as claimed in claim 1, wherein said second end is substantially pyramidal and has a four-sided base.

5. Needle as claimed in claim 4, wherein said four-sided base is substantially square.

6. Needle as claimed in claim 1, wherein the substantially conical or pyramidal shape of the core is blunted by application of a blunting force to the second end of the needle.

7. Needle as claimed in any of the preceding claims, wherein the outer cannula comprises stainless steel.

8. Needle as claimed in claim 1, wherein the insulating layer comprises polyesterimide.

9. Needle as claimed in claim 1, further comprising a receiving socket having a conducting inner wall electrically connected to the outer cannula.

10. Needle probe, comprising a needle as claimed in claim 1 and a further part, wherein the needle is selectively engageable with said further part, said further part having an electrical connector, first means to provide electrical connection between the core and a first connection point of the electrical connector on engagement of the needle with the further part, and second means to provide electrical connection between the outer cannula and a second connection point of the electrical connector on engagement of the needle with the further part.

11. Needle probe as claimed in claim 10, wherein said first means comprises a spring contact probe adapted to press against the core at said second end of the needle when the needle is engaged with said further part of the needle probe.

12. Needle probe as claimed in claim 11, wherein said spring contact probe is adapted to press against said core with a force lying in the range of 52 to 108 gf.

13. Needle probe as claimed in claim 10 where dependent on claim 10, wherein said second means comprises a plurality of resilient fingers adapted to bear against the conducting inner wall of the receiving portion of the needle when the needle is engaged with the further part of the needle probe.

14. Needle probe as claimed in claim 13, wherein said second means comprises six resilient fingers.

15. Needle probe as claimed in claim 10 and adapted for use in electromyography.

\* \* \* \* \*